(12) United States Patent
D'Anniballe et al.

(10) Patent No.: US 8,962,555 B2
(45) Date of Patent: Feb. 24, 2015

(54) PLGF-1 IN HOMODIMERIC FORM

(75) Inventors: Gaetano D'Anniballe, L'Aquila (IT); Franck Martin, L'Aquila (IT); Giuseppe Salvia, Catania (IT)

(73) Assignees: Dompe S.p.A., L'Aquila (IT); Geymonat S.p.A., Anagni (IT)

( * ) Notice: Subject to any disclaimer, the term of this patent is extended or adjusted under 35 U.S.C. 154(b) by 0 days.

(21) Appl. No.: 13/394,715

(22) PCT Filed: Sep. 9, 2010

(86) PCT No.: PCT/EP2010/063217
§ 371 (c)(1),
(2), (4) Date: May 23, 2012

(87) PCT Pub. No.: WO2011/029861
PCT Pub. Date: Mar. 17, 2011

(65) Prior Publication Data
US 2012/0232008 A1  Sep. 13, 2012

(30) Foreign Application Priority Data
Sep. 9, 2009 (EP) ..................... 09169873

(51) Int. Cl.
*A61K 38/18* (2006.01)
*C07K 14/475* (2006.01)
*C07K 14/515* (2006.01)

(52) U.S. Cl.
CPC .................................. *C07K 14/515* (2013.01)
USPC ............................. 514/8.1; 530/399; 530/402

(58) Field of Classification Search
None
See application file for complete search history.

(56) References Cited

U.S. PATENT DOCUMENTS

2005/0070696 A1  3/2005  Maglione et al.
2005/0176634 A1  8/2005  Maglione et al.

FOREIGN PATENT DOCUMENTS

WO  03/066676  8/2003
WO  03/097688  11/2003

OTHER PUBLICATIONS

Cao et al. "Placenta growth factor: Identification and characterization of a novel isoform generated by RNA alernative splicing" *Biochemical and Biophysical Research Communications*, vol. 235, No. 3, pp. 493-498 (Jun. 1997).

Iyer et al. "The crystal structure of human placenta growth factor-1 (P1GF-1), an angiogenic protein, at 2.0 Å resolution" *Journal of Biological Chemistry*, vol. 276, No. 15, pp. 12153-12161 (Apr. 2001).

Yang et al. "Evidence of a novel isoform of placenta growth factor (P1GF-4) expressed in human trophoblast and endothelial cells" *Journal of Reproductive Immunology*, vol. 60, No. 1, pp. 53-60 (Oct. 2003).

*Primary Examiner* — Christine J Saoud
(74) *Attorney, Agent, or Firm* — Nixon & Vanderhye PC

(57) ABSTRACT

The present invention relates to a new homodimeric form of recombinant PlGF-1, to a process for its preparation and to compositions containing it.

26 Claims, 9 Drawing Sheets

PLGF-1 IN HOMODIMERIC FORM

This application is the U.S. national phase under 35 USC 371 of Int'l Application No. PCT/EP2010/063217, filed 9 Sep. 2010, which designated the U.S.; and claims priority to EP Application No. 09169873.8, filed 9 Sep. 2009; the entire contents of which is hereby incorporated by reference.

TECHNICAL FIELD

The present application relates to a new homodimeric form of PlGF characterized by the presence in its C-terminal region of one inter-chain disulfide bonds. The present application further relates to a process for its production and purification, compositions comprising the same and its use as a medicament or a cosmetic agent. The application also relates to other objects, which will be evident from the description.

BACKGROUND

Placental Growth Factor (PlGF) is a member of Vascular Endothelial Growth Factor (VEGF) family and acts as angiogenic amplifier by signaling through VEGF receptor-1, expressed mainly by vascular endothelial cells, monocytes, macrophages, but also by human CD34+ marrow repopulating stem cells.

PlGF occurs in at least four splicing isoforms, PlGF-1 to PlGF-4 that differ in size and binding properties.

The complete peptide and nucleotide sequence of PlGF-1 has been described in patent application WO 92/06194.

In details, PlGF-1 sequence contains nine cysteine residues in position 35, 60, 66, 69, 70, 77, 111, 113 and 125 that are potential candidates for the formation of intra- and inter-chain disulfide bonds. The above numbering of the cysteine residues is relative to recombinant PlGF-1 produced in *Escherichia coli* which comprises an N-terminal Methionine not present in native PlGF-1 (for example: $Cys^{35}$ in the recombinant PlGF-1 corresponds to $Cys^{34}$ in native PlGF-1—also known as $PlGF_{131}$).

The presence of disulfide bonds has been confirmed by the analysis of the crystal structure of PlGF-1 at 2.0 Å resolution (Iyer S. et al., *J. Biol. Chem.*, 2001, 276, 12153-12161). According to Iyer et al., PlGF-1 is described as a homodimeric molecule organized in an antiparallel arrangement covalently linked by two interchain disulfide bonds between $Cys^{60}$-$Cys^{69}$ $Cys^{69}$-$Cys^{60}$ and three intrachain disulfide bonds: $Cys^{35}$-$Cys^{77}$, $Cys^{66}$-$Cys^{111}$ and $Cys^{70}$-$Cys^{113}$.

The most relevant feature evidenced by the crystallographic analysis is the presence of a cysteine-knot motif. The C-terminal sequence of PlGF-1, following the position 114, does not show an organized structure and, by consequence, the related crystal structure has not been defined.

Yet, the distance existing between the two cysteine residues in position 125 in the homodimer renders the presence of an interchain covalent bond between these two positions unlikely, since this would require a distortion of the molecule.

The homodimeric form has been shown to be the biologically active form of PlGF, while the monomer of PlGF is inactive.

A number of studies have evidenced the pharmacological activity of PlGF-1.

For example, preliminary observations have shown positive effects obtained by an adenoviral vector expressing hPLGF (human Placental Growth Factor) on early and late bone marrow hematopoiesis in 5-fluorouracil-suppressed mice and in the mobilization of stem/progenitor cells into the bloodstream.

Furthermore, PlGF-1 has been shown to induce angiogenesis in vivo and to stimulate the migration and proliferation of endothelial cells in vitro (Ziche M. et al., *Lab. Invest.*, 1997, 76, 517-531). A beneficial effect of PlGF protein or gene therapy on ischemic conditions has been disclosed in e.g. WO-A-01/56593 and US-2007/0027100. The ischemic conditions include cerebral ischemia, acute myocardial infarction and ischemic hind limb.

Patent Application WO-A-03/066676, herein enclosed by way of reference, describes a process for the extraction and purification of recombinant PlGF-1 from genetically modified bacterial cells. The product obtained, hereinafter referred to as [DIM1/2] PlGF-1, comprises at least 98.5% of dimeric and multimeric active forms, at least 70% of dimeric form and less than 1.5% of the monomeric form, which is inactive.

According to this process, PlGF-1 is expressed as inclusion bodies in *E. coli* by recombinant DNA technology. Then it is extracted by solubilization of the inclusion bodies in a denaturant buffer, it is refolded in the presence of a redox system and subsequently purified by a two steps chromatography procedure (anionic exchange chromatography followed by reverse phase chromatography).

Although the PlGF-1 protein obtained with the process disclosed in WO-A-03/066676 is a highly pure active form, the present inventors have found that this product does not exhibit optimal stability in aqueous solution and sometime shows batch-to-batch heterogeneity (by Mass spectrometry, SDS-PAGE and IEF analysis).

WO-A-03/097688 discloses the preparation of a mutein of the PlGF-1 molecule, wherein the cysteine in position 125 of the PlGF-1 molecule has been replaced by a different amino acid unable to form disulphide bonds.

The above mutein shows a better stability in aqueous solution than the wild-type PlGF-1.

Scope of the present invention is to provide a new stabile form of active PLGF.

SUMMARY OF THE INVENTION

The present inventors have produced a novel active PLGF homodimer, exhibiting unexpected properties of reproducibility and stability and a new process for its preparation.

Accordingly, the object of an embodiment of the invention is a new homodimeric form of PlGF having an interchain disulfide bond between two cysteine residues in the C-terminal region of each monomer protein. Beyond the C-terminal interchain bond, the dimer may have one or two additional interchain bonds. In a realization form of this object, said C-terminal disulfide bridge is between two Cys-residues at a position in each monomer selected from: position 125 of recombinant PLGF-1, position 124 of $wtPLGF_{131}$, position 146 of recombinant PLGF-2, position 145 of $wtPLGF_{152}$, position 197 of recombinant PLGF-3, position 196 of $wtPLGF_{203}$, position 218 of recombinant PLGF-4, position 217 of $wtPlGF_{224}$.

A specific realization form of this object is a recombinant PLGF-1 dimer, which may have three interchain disulfide bonds and it is referred to as [DIM3]PLGF-1. In a even more specific realization form of this object, the interchain disulfide bonds are between residues $Cys^{60}$-$Cys^{69}$, $Cys^{69}$-$Cys^{60}$ and $Cys^{125}$-$Cys^{125}$.

Object of another embodiment of the invention is a process for the preparation of said PlGF homodimer comprising the steps of obtaining the PlGF monomer protein, allowing said monomer to oxidize by incubating it in a buffer, and by removing any reducing agents, if present, so obtaining the desired PLGF homodimer and optionally purifying said PLGF homodimer.

In a realization form of this embodiment, PlGF monomer is obtained by the step of incubating the PlGF homodimer, containing less than three disulfide interchain bridges, in a buffer containing a reducing agent and having pH from neutral to weakly basic.

Objects of other embodiments of the invention are the PlGF homodimer according to the invention, for use in medical treatments, such as promoting mobilisation of blood stem cells in subjects in need thereof, treating ischemic diseases, cutaneous scleroderma or progressive systemic scleroderma, skin ulcers, wounds, burns, post-operative situation, natural or precocious ageing of the cutaneous tissues, and any pathological hair loss.

Objects of still other embodiments of the invention are pharmaceutical compositions comprising the PLGF of the invention.

Other objects of the invention will be apparent in the light of the detailed description below.

The presence of more than two interchain disulfide bond in the PlGF dimeric molecule, one of which between two C-terminal cysteine residues, has never been described before. This finding is particularly surprising and unexpected in view of the published crystal structure of the dimeric protein, which is organized in an antiparallel arrangement. For this reason, the distance between the two C-terminal cysteine is such that the formation of the disulfide bridge would require a dramatic distortion of the molecule conformation. Therefore the formation of the third disulfide bridge was completely unpredictable since based on an unfavorable conformation of the monomers.

Yet, as shown in the experimental section, the complete structural and functional characterization of the obtained product, proved not only its feasibility, but also its higher stability and higher batch-to-batch reproducibility compared to known homodimers having less than three disulfide bonds, i.e. [DIM1/2]PlGF-1. Moreover, the new form of PlGF-1 unexpectedly displays an improved biological activity as compared to the known dimer.

DETAILED DESCRIPTION OF THE INVENTION

Figure 1:
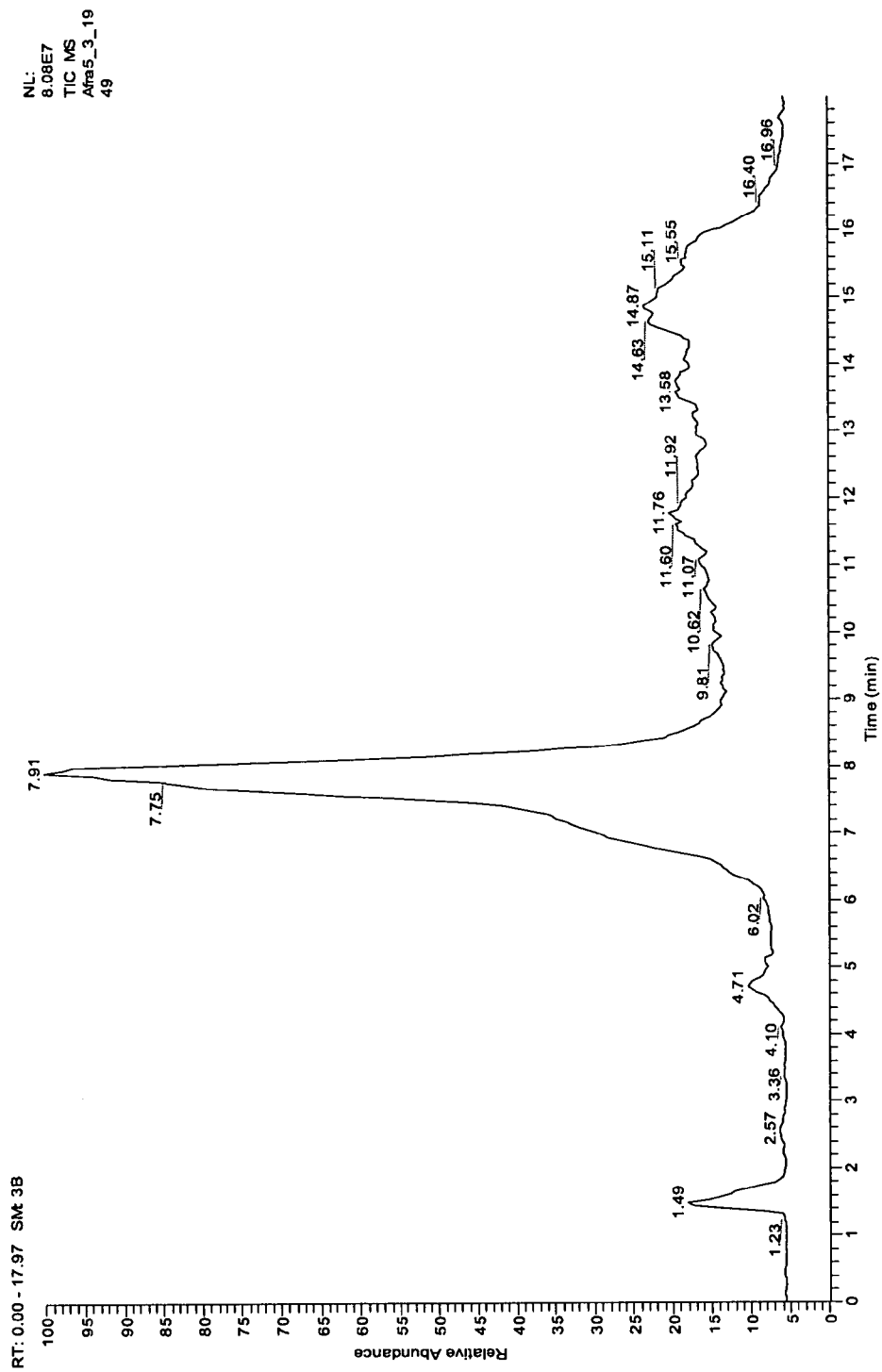
FIG. 1 shows a RP-LC-MS chromatogram of [DIM1/2] PlGF-1.

The PLGF homodimer according to the present invention may be any one of the known PLGF types, namely PLGF-1, PLGF-2, PLGF-3 or PLGF4.

The C-terminal cysteine residues of two monomeric PlGF proteins are involved in an intermonomer disulfide bond.

The expression "intermonomer" and "interchain" are considered equivalent and changeable.

The expression "disulfide bridge" and "disulfide bond" are also considered equivalent and changeable.

The expression "C-terminal" according to the present invention, means the monomer C-terminal region comprising only one and the last cysteine residue. Such residue, involved in the inter-chain bond, is at position 125 of recombinant PLGF-1 (corresponding to position 124 in wtPlGF$_{131}$), at position 146 of in recombinant PlGF-2 (corresponding to position 145 in wtPlGF$_{152}$), at position 197 in recombinant PlGF-3 (corresponding to position 196 in wtPlGF$_{203}$), and at position 218 in recombinant PlGF-4 (corresponding to position 217 in wtPlGF$_{224}$). Accordingly, the homodimers of the invention comprise one interchain disulfide bond at Cys$^{125}$-Cys$^{125}$ in PLGF-1, at Cys$^{146}$-Cys$^{146}$ in PLGF-2, at Cys$^{197}$-Cys$^{197}$ in PLGF-3 or at Cys$^{218}$-Cys$^{218}$ in PLGF-4. In one exemplifying embodiment of the invention the homodimer is an isolated PlGF-1 protein homodimer having three interchain disulfide bridges. According to a specific form of the invention the bridges are between the two monomers, preferably between Cys$^{60}$-Cys$^{69}$, Cys$^{69}$-Cys$^{60}$ and Cys$^{125}$-Cys$^{125}$. This new PlGF-1 protein will be hereinafter referred to as [DIM3]PlGF-1.

The term "monomer of PlGF" according to the present invention means either a monomeric protein in native form (w.t.), i.e. monomer PlGF$_{131}$, monomer PlGF$_{152}$, monomer PlGF$_{203}$ or monomer PlGF$_{224}$, or a recombinant monomer protein expressed in modified host cells. The PlGF monomer may be non-glycosylated, if expressed in prokaryotic cells, such as bacteria, as disclosed in WO-A-92/06194 or in WO-A-03/066676, or at least partially glycosylated if expressed in eukaryotic cells, such as yeast or mammalian cells.

The presence of an additional inter-chain disulfide bond confers novel and unexpected properties to the homodimers of the invention, as regard to the known PLGF dimers.

For example, as demonstrated in more details in the experimental section, the product of the invention is endowed with a higher stability and is substantially more homogeneous as compared to the known [DIM1/2]PlGF-1, having only two interchain disulfide bonds involving Cys$^{60}$ and Cys$^{69}$.

Furthermore, the new homodimer surprisingly shows a higher intrinsic activity in in vitro chemotaxis assay that correlates with an improved in vivo efficacy compared to [DIM1/2]PlGF-1.

A further aspect of the present invention is a process for the preparation of a PlGF homodimer, for example the [DIM3] PlGF-1.

This process comprises the following steps:
I. Obtaining the PlGF monomer protein,
II. oxidizing or allowing said monomer to oxidize to obtain the PLGF homodimer, and optionally
III. purifying the PLGF homodimer.

Step I:

A number of different procedures can be followed in step I in order to obtain monomeric PlGF, preferably all preserving the native structure of the intrachain disulfide bonds.

According to an embodiment of the invention, step I comprises the preparation of monomeric PlGF from a homodimeric form of PlGF lacking the interchain disulfide bridges between the C-terminal cysteine residues. In this case step I comprises the following steps:

incubating a homodimeric form of PlGF in a buffer having from neutral to basic pH, for example ranging from 7 to 9.5 and containing a reducing agent, then eliminating or inactivating the reducing agent, according to the procedures described below.

When the starting product is the homodimeric form of PlGF-1, this will contain less than three interchain disulfide bonds. For example homodimers with one or two disulfide bonds or mixture thereof may be used. The preferred starting product is the homodimeric form [DIM1/2]PlGF-1 which is obtained according to the process described in WO-A-03/066676.

Any type of reducing agents commonly employed for protein chemistry may be used in this step of the process. For example, Tris(2-Carboxyethyl) phosphine hydrochloride (TCEP*HCl), Dithiothreitol (DTT) or equivalent agents or mixture thereof.

The reducing agent is preferably used at a molar ratio: reducing agent/PLGF protein in the range 5:1-100:1, and the incubation with said reducing agent is carried out for a time comprised between 10 min and 30 hours, preferably between 30 minutes and 2 hours.

According to an alternative embodiment, step I comprises the preparation of monomeric PlGF from inclusion bodies obtained in bacterial host cells by recombinant DNA technology, containing the PlGF-1 molecule. The inclusion bodies are preferably obtained according to the process described in WO-A-03/066676. In this case step I comprises the following steps:

incubating an inclusion bodies containing PlGF in a buffer having from neutral to basic pH, for example ranging from 7 to 9.5, preferably Tris buffer (pH 8), and containing a denaturing agent as, for example urea 8M or guanidine 6 M, optionally in the presence of cahotropic agents (such as ethylen diamine, Arginine, etc);

reducing the protein solution thus obtained with a reducing agent;

Any type of reducing agents commonly employed for protein chemistry may be used in this step of the process. For example, Tris(2-Carboxyethyl) phosphine hydrochloride (TCEP*HCl), Dithiothreitol (DTT) or equivalent agents or mixture thereof.

Preferably, the reducing agent is used The reducing agent is preferably used at a molar ratio: reducing agent/PLGF protein in the range 5:1-100:1, and the incubation with said reducing agent is carried out for a time comprised between 10 min and 30 hours, preferably between 30 minutes and 2 hours.

The so obtained monomer may be either in completely reduced form or, preferably, it maintains its native folding by preserving all intrachain disulfide bonds.

After reduction, the obtained monomer can be directly submitted to step II oxidation without any preliminary purification.

In this case, it is desirable to carry out a purification step III in order to obtain purified final homodimeric PlGF.

Not purified PLGF monomer means, according to the invention, a protein mixture containing from 50% to 90% of the monomer.

Alternatively, the obtained monomer may be submitted to a preliminary purification, before oxidation. Monomeric PlGF-1 in purified form means, according to the present invention, a protein mixture containing at least 90%, preferably at least 95% and more preferably at least 98% or more of the PlGF monomer.

When the oxidation step is carried out on a purified monomer, for instance PlGF-1 monomer, the oxidation normally results in a purified homodimer, e.g. [DIM3]PlGF-1, which need no further purification step III.

Step II

After reduction, the obtained monomer can be submitted to step II oxidation by eliminating or inactivating the reducing agent and/or the denaturant with suitable techniques, such as by dialyzing, by adequately diluting, for example, by 10 to 100 times, or by any other means, such as chromatography.

In a first alternative, the oxidation is carried out on the non purified monomeric PlGF. Usually, the solution is sufficiently diluted to prevent the reducing agent and, when present, the denaturing agent from reacting with the thiol groups of the cysteine residues and/or interfering with the protein folding.

If this is not the case, before performing step II, the reducing agent and, when present, the denaturing agent must be removed from the above solution or alternatively inactivated towards the reaction with free cysteines and interference with the folding of the protein, as described hereinafter.

Any known technology suitable for purifying protein material, may be used in this stage of the process. Techniques that may be used are for example filtration, chromarographic purification comprising ionic exchange chromatography and/or gel exclusion chromatography. As well known, some of these techniques cause the elimination of the small molecules only, for example the reducing agent, while other cause also the elimination of protein contaminants.

In order to obtain the desired homodimeric PlGF protein, the monomer is allowed to oxidize by incubating it in a buffer having a pH ranging from neutral to basic values and in the absence of any reducing agent and in the absence of any denaturing agent capable of interfering with the oxidation of the cysteine residues of the monomeric PlGF. If the PlGF is PlGF-1, then the product of oxidation, i.e. the homodimer, normally comprises three interchain disulfide bonds: i.e. [DIM3]PlGF-1.

By "absence of reducing agents" according to the present invention, it is meant either the absolute absence of reducing agents or the presence of reducing agents in such amounts or conditions that they cannot interfere with the oxidation of the thiol groups of the cysteine residues of the PlGF monomer.

By "absence of denaturing agent" according to the present invention, it is meant either the absolute absence of denaturing agents or the presence of denaturing agents in such amounts or conditions that they cannot interfere with the folding of the protein.

For the complete formation of all interchain disulfide bonds, comprising the C-terminal disulfide bond, the oxidation is preferably carried out simply under air atmosphere. Alternatively, small amounts of oxidising agents can be added to render oxidation more rapid. In this latter case, the formation of protein multimers can easily be avoided by simple control of the amount of oxidising agents. The oxidation time normally varies from 12 and 48 hours. The reaction is carried out at a temperature between 15° C. and 30° C., preferably at room temperature. The buffer in which the oxidation process takes place may be any buffer having a pH neutral to basic, in particular from pH 7 to pH 9.5, for example pH 7.2, pH 8.3 or pH 9. Suitable Buffers are selected from sodium phosphate buffer, TRIS.HCl buffer, ammonium phosphate buffer or any equivalent buffer. Finally, the monomeric PlGF is reacted at initial concentration ranging from 3 to 10 mg/mL solution.

If the step of obtaining the PLGF monomer involves the use of a reducing agent, this agent must be eliminated or inactivated from the oxidation solution completely or at least to the extent that it does not interfere with the oxidation.

The elimination of the reducing agent is carried out by replacing the buffer with a buffer having from neutral to basic pH, for instance between 7 and 9.5, not containing any reducing agent. Alternatively, the elimination of the reducing agent is at least partially achieved by way of one or more chromatographic purification steps, for example by any type of ionic exchange chromatography, gel filtration chromatography and hydrophobic interaction chromatography in any order. For example, one anion- or cation-exchange chromatography followed by a gel filtration and/or a hydrophobic interaction chromatography.

The chromatografic way of eliminating the reducing agent offers the additional advantage of enabling a concomitant purification, or an additional purification, of the PLGF monomer protein from any other protein material.

Finally the reducing agent may be inactivated by diluting of the protein solution and/or by adding to said solution an excess of any oxidizing agent known in the art as suitable to be used in the presence of proteins.

Step III:

The purpose of step III is to have a final homodimer at a level of purity not less than 90%, preferably at least 95% and more preferably at least 98%.

Usually, the purification of step III consists of one or more chromatografic purifications. Preferably, said chromatographic purifications comprise a ionic exchange chromatography, optionally, followed by a size exclusion chromatography and/or hydrophobic interaction chromatography.

The opportunity to carry out the purification step III depends on the purity of the monomeric PlGF obtained in step I and on the purity of the final product that it is desired to achieve.

As shown in the Experimental section, the process of the invention, when carried out on PLGF-1, leads to a pure, stable and highly active homodimer, mainly having three interchain disulfide bonds between the monomer residues $Cys^{60}$-$Cys^{69}$, $Cys^{69}$-$Cys^{60}$ and $Cys^{125}$-$Cys^{125}$.

The presence of a biological/pharmacological activity in the obtained product has been assessed by chemotaxis experiments performed on human monocytes and in animal models, BALB/c mice (see Examples 9 and 10). [DIM3]PlGF-1 has been compared with [DIM1/2]PlGF-1 in both the above experiments.

Figure 8:
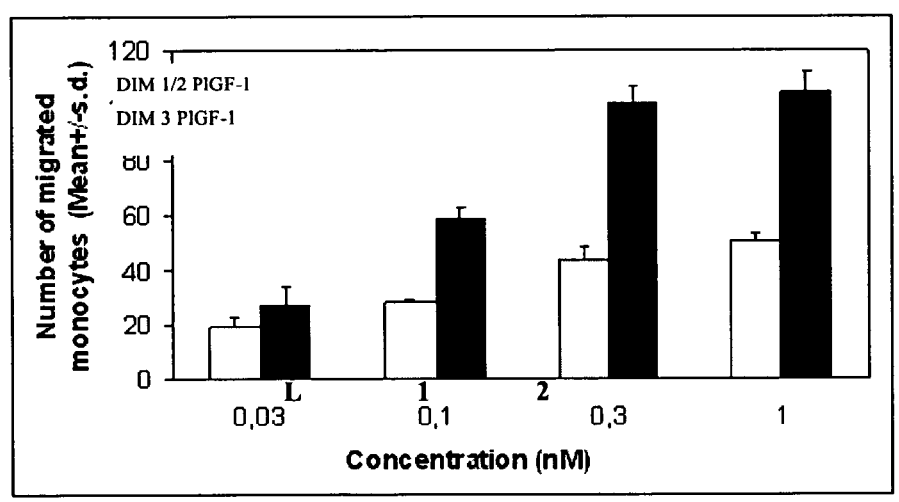
FIG. 8 is a histogram showing the chemotactic activity at increasing concentrations of [DIM1/2]PlGF-1 or [DIM3] PlGF-1.
Figure 9:
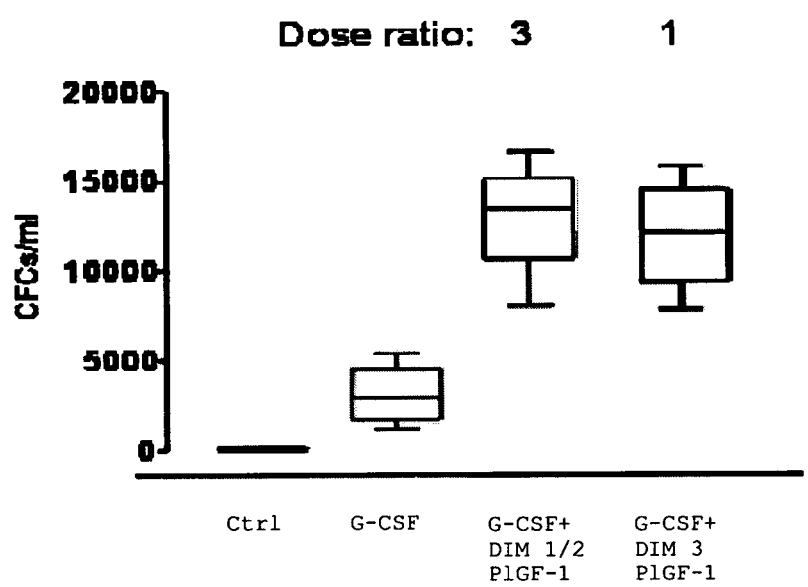
FIG. 9 shows the effect of a 12-day mobilization obtained with G-CSF alone or G-CSF in combination with [DIM1/2] PlGF-1 or [DIM3]PlGF-1.
Figure 10:
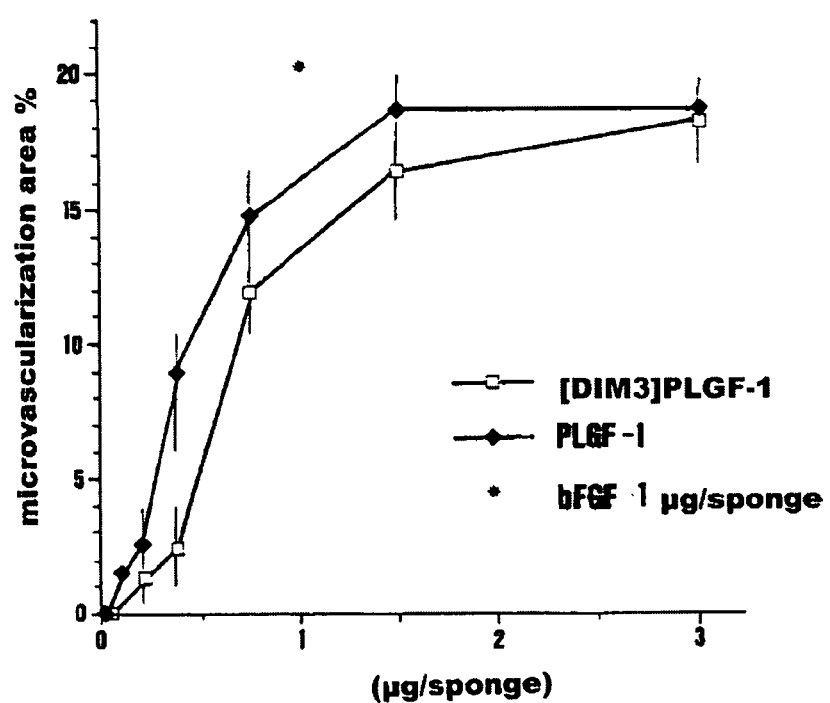
FIG. 10 shows the comparison of the angiogenic activity of the [DIM3]PlGF-1, of the [DIM1/2]PLGF-1 and, as a positive reference, of the basic fibroblast growth factor (bFGF) using the chicken chorioallantoid membrane vascularization test (CAM).

The results obtained and shown in FIGS. 8 and 9 and 10 demonstrate not only that [DIM3]PlGF-1 exerts an angiogenic activity, a chemotactic activity and a cell colony formation activity, but also that the intrinsic activity, that is the ability to activate the biological stimulus, is higher than that observed with [DIM1/2]PlGF-1.

These biological effects reflect all the pharmacological properties and therapeutic applications known in the art for the wild type PLGF as well as for the recombinant PLGF produced according to the earlier WO-A-2003/066676 and WO-A-2003/097688.

The present invention also relates to the use of new homodimeric PlGF for the preparation of medicaments promoting the mobilization of blood stem cells in patients or subjects in need thereof. Examples of patients that may benefit from the use of the medicament of the invention are patients undergoing chemotherapy.

Moreover, new homodimeric PlGF, having angiogenic activity, is used in the therapeutic treatments of ischemic diseases such as ischemia of the myocardial tissue, myocardial infarct, ischemic ictus and chronic ischemic myocardial diseases cerebral ischemia and ischemic ictus, intestinal ischemia, peripheral ischemia of the limbs. Additionally it is used in the treatment of scleroderma, in the treatment of skin ulcers, wounds, burns, post-operative treatment, in the treatment of natural or precocious ageing of the cutaneous tissues and in the treatment of natural or pathological hair loss.

In view of its stability and purity profile, the dimer of the invention is highly suitable for manufacturing in the pharmaceutical industry.

Accordingly, a still further object of the invention relates to compositions comprising a homodimeric PlGF according to the invention in admixture with at least one pharmaceutically acceptable carrier, excipient, diluent or adjuvant.

Any formulation suitable for the systemic or local administration of therapeutic agents may be used in accordance with the invention. Formulations for local use are used in the field of cosmetic applications.

In particular, the new homodimer may be administered by parenteral route with a systemic or local effect, or by topic route on skin or mucosae, with a mainly local effect. A systemic effect is mainly achieved by endovenous administration, though intraperitoneal or intramuscular administration are suitable as well. A local effect is achieved via topic, or parenteral intramuscular, subcutaneous, intrarticular administration. Likewise, the PLGF-1 factor may be locally administered via electrotransport or ionophoresis. The oral administration of the factor, is less advisable in view of the active product sensitivity.

Compositions for parenteral, systemic or local use comprise solutions, suspensions, liposome suspensions, W/O or O/W emulsions. Compositions for topical use comprise solutions, lotions, suspensions, liposome suspensions, W/O or O/W emulsions, gels, ointments, creams, pomades and pastes. In a preferred embodiment the active substance is formulated in a lyophilised form, mixed to suitable lyophilisation additives and ready for reconstitution with therapeutically acceptable diluents. Useful lyophilisation additives are: buffers, polysaccharides, suchrose, mannitol, inositol, polypeptides, amino acids and any other additive compatible with the active substance. In a preferred embodiment of the invention the active substance is dissolved in phosphate buffer ($NaH_2PO_4/H_2O$—$Na_2HPO_4/2H_2O$) in an amount such that the post-lyophilisation PLGF1/phosphate ratio is comprised between 1:1 and 1:2. Diluents suitable for parenteral use are: water, physiological solutions, sugar solutions, hydroalcoholic solutions, oily diluents, polyols, like glycerol, ethylene or polypropylene glycol, or any other diluent compatible with the administration method as for sterility, pH, ionic strength and viscosity.

In the case of emulsions or suspensions, the composition may contain suitable surfactants of non-ionic, zwitterionic, anionic or cationic type commonly used in the formulation of medicaments. Oil/water (O/W) hydrophilic emulsions are preferable for parenteral systemic use, whereas water/oil (W/O) lipophilic emulsions are preferable for local or topic use.

Moreover, the compositions of the invention may contain optional additives like isotonic agents, such as sugars or polyalcohols, buffers, chelating agents, antioxidants, antibacterials.

The compositions for topic use comprise liquid forms or semisolid forms. The liquid forms comprise solutions or lotions. These may be aqueous, hydroalcoholic, like ethanol/water, or alcoholic and are obtained by solubilising the lyophilised substance.

Alternatively, active substance solutions may be formulated in form of gel by addition of known gelling agents, like: starch, glycerin, polyethylene or polypropylene glycol, poly(meth) acrylate, isopropyl alcohol, hydroxystearate.

Other types of compositions for topic use are emulsions or suspensions in form of pomades, pastes, creams. W/O emulsions are preferable, providing a faster absorption. Examples of lipophilic excipients are: liquid paraffin, anhydrous lanolin, white vaseline, cetyl alcohol, stearyl alcohol, vegetable oils, mineral oils. Agents increasing cutaneous permeability, thereby facilitating the absorption, may advantageously be used. Examples of such agents are physiologically acceptable additives like polyvinyl alcohol, polyethylenglycol or dimethylsulfoxide (DMSO).

Other additives used in the topic compositions are isotonic agents, like sugars or polyalcohols, buffers, chelating agents, antioxidants, antibacterials, thickeners, dispersants.

Likewise, delayed-release compositions for local or systemic use may be useful, and comprise polymers like polylactate, poly(meth)acrylate, polyvinylpyrrolidone, methylcellulose carboxymethylcellulose and other substances known in the art. Delayed-release compositions in form of subcutaneous implants based on, e.g. polylactate or other biodegradable polymers may be useful as well.

Though the active substance is preferably packaged in lyophilized and hence stable form, the pharmaceutical compositions advantageously comprise substances stabilizing the homodimer in the active dimeric forms.

EXPERIMENTAL SECTION

Example 1

Characterization of [DIM1/DIM2]PlGF

A sample of [DIM1/2]PlGF-1, obtained according to the procedure described in WO03/066676 at a concentration of 1 mg/ml in a $NaH_2PO_4$ buffer solution (pH 7.2) was injected into a C18 analytical column in gradient conditions followed by ESI-MS analysis.

Analytical conditions: ThermoFinnigan LTQ Ion Trap equipped with MicroHPLC system;
C18 HPLC column;
Elution system: System A: $H_2O/CH_3CN/HCOOH$ 97:2:1
System B: $H_2O/CH_3CN/HCOOH$ 2:97:1
Elution gradient:
t=0 System A/System B 80:20
t=12 min System A/System B 50:50
t=15 min System A/System B 50:50
t=16 min System A/System B 80:20
The obtained TIC chromatogram is shown in FIG. 1.

The chromatogram shows a main peak of [DIM1/2]PlGF-1 at rt=7.91 min. The related multicharge and deconvoluted MS spectra (FIGS. 2 and 3, respectively) prove the presence of several different species of PlGF-1 in the sample.

Figure 2:
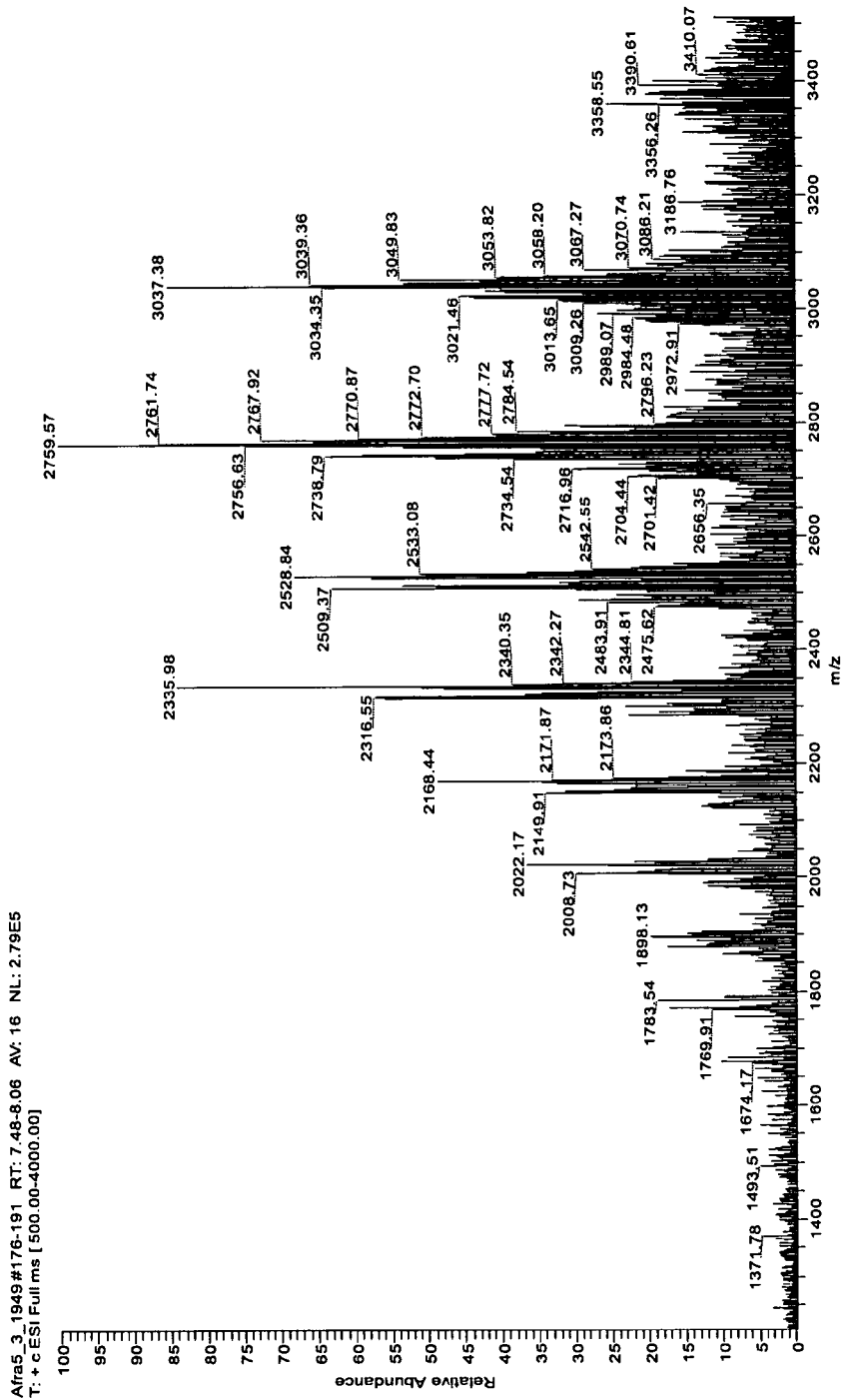
FIG. 2 shows a Multicharge MS spectrum of [DIM1/2] PlGF-1.

FIG. 2, illustrates the presence of a broad panel of proteins.

Figure 3:
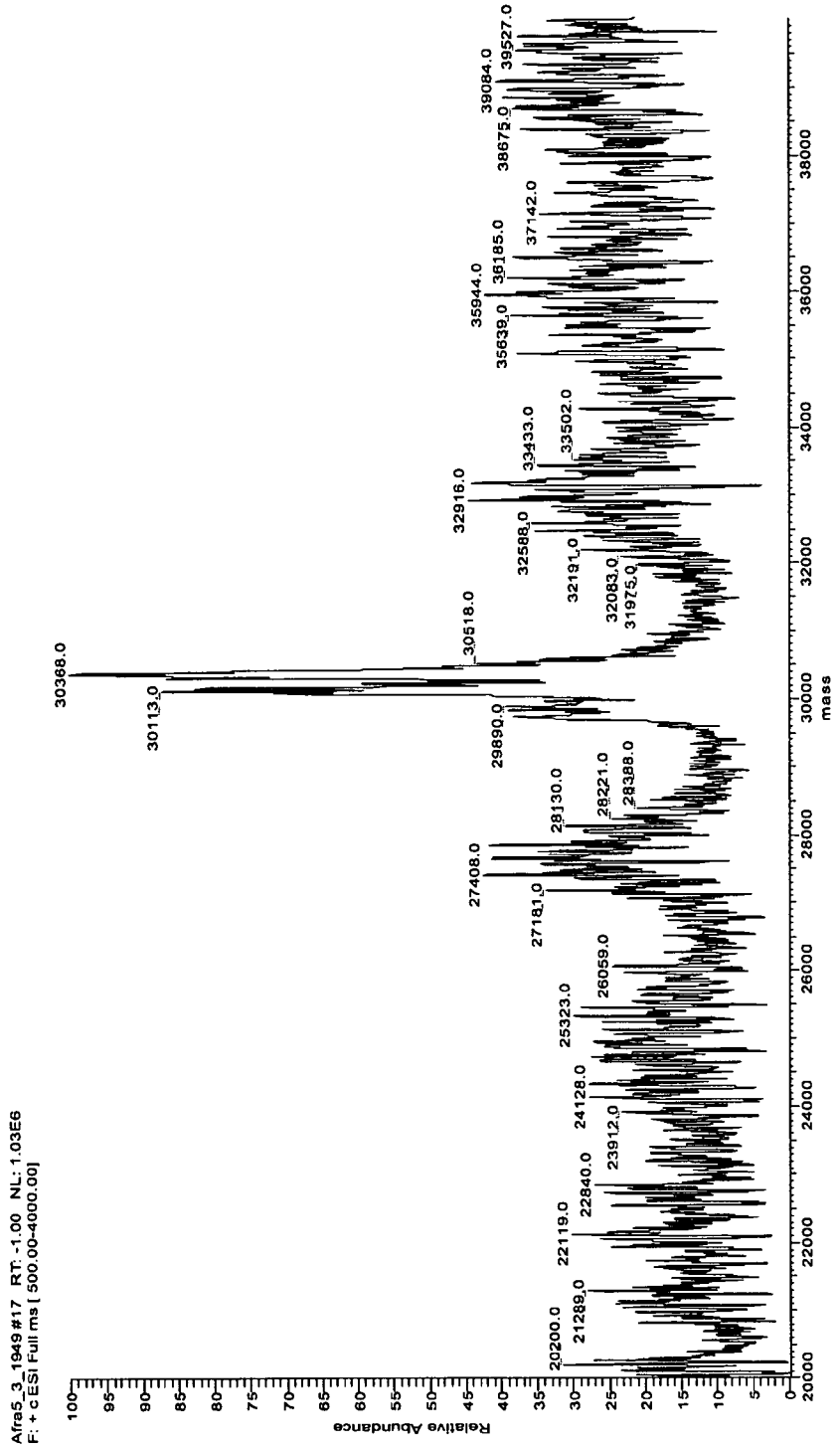
FIG. 3 shows a deconvoluted mass spectrum of [DIM1/2] PlGF-1.

FIG. 3 shows in detail that the species [DIM1/2]PlGF-1 is indeed a mixture of proteins with molecular weight in the range 29.7-30.5 KDa.

The data obtained substantiate the presence of the expected dimeric protein of MW 29690, together with more abundant variants having higher molecular weight, some of them accounting for the presence of small organic molecules covalently linked to cysteine residues of the molecule.

Example 2

Production of [DIM3]PlGF-1

2.5 mL of purified DIM1/2 PlGF-1, according to WO-A-03/066676, (conc. 0.9 mg/mL, pH 7.2) was loaded on PD-10 desalting columns in order to carry out a buffer exchange. The sample was eluted with 3 mL of 50 mM $NH_4H_2PO_4$ buffer at pH 9 (protein conc. 0.75 mg/mL). 2.5 mL of the obtained solution was reduced with 12 µL of dithiotreitol (DTT) (4 mg/mL), thus establishing a reducing agent/protein molar ratio of 5/1 (reduction time: 30 min). As a result of this reaction, the interchain disulfide bridges were reduced, while intrachain disulfide bridges remained intact, and PlGF in monomeric form was obtained. The reduced protein solution (2.5 mL) was then loaded on PD-10 columns in order to eliminate the reducing agent, and eluted with 3 mL of 50 mM $NH_4H_2PO_4$ buffer at pH 9. The obtained eluate was incubated for 18 hours at room temperature.

Characterization of the Product

A LC-MS analysis was performed on a sample of 0.62 mg/ml of [DIM3]PlGF-1 obtained in the above process. In details, the sample was injected into a C18 analytical column in gradient conditions performed by HPLC-MS analysis, according to the same procedure used foe [DIM1/2] PlGF-1 in Example 1.

Figure 4:
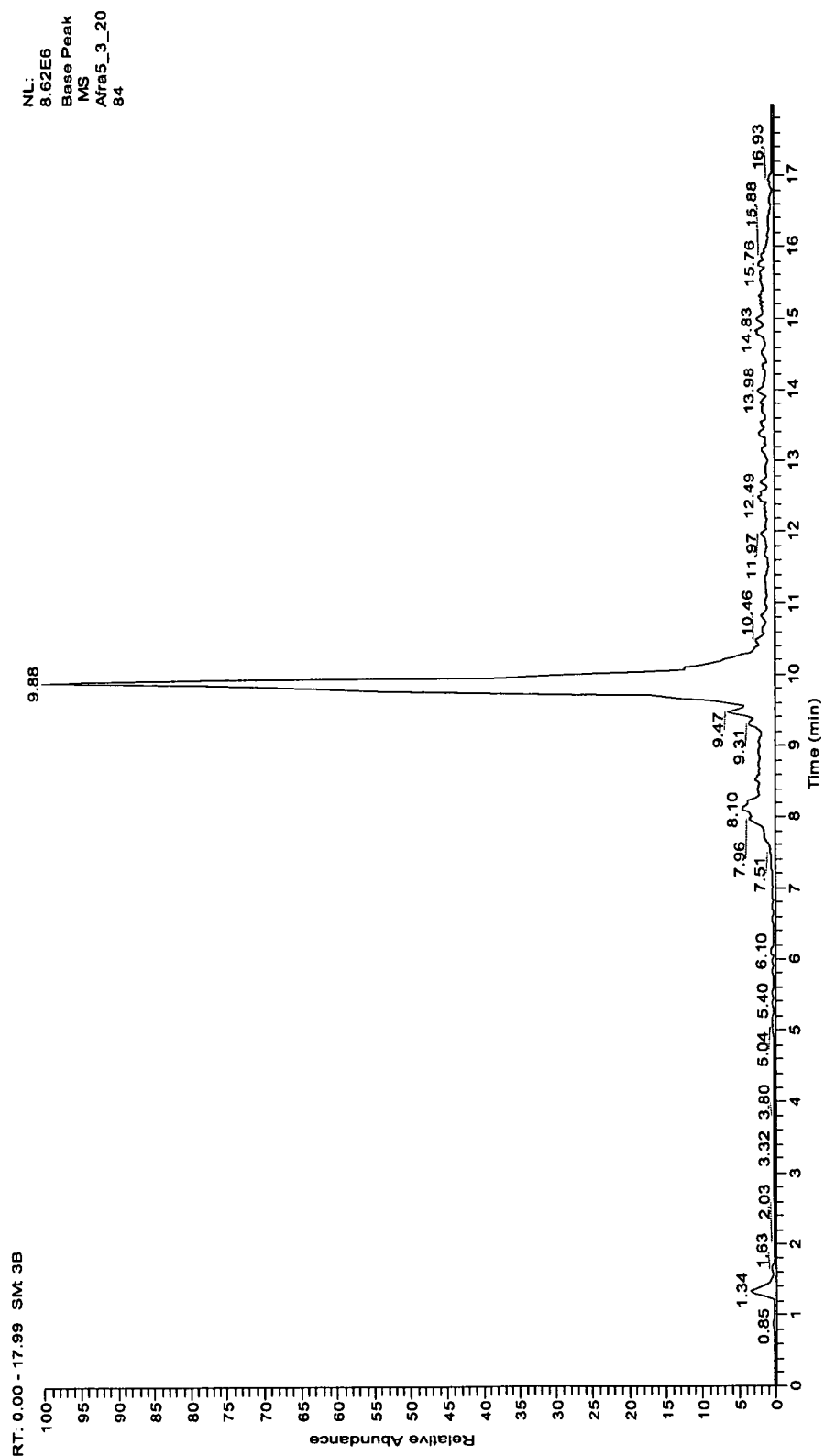
FIG. 4 shows RP-LC-MS chromatogram of [DIM3]PlGF-1.
Figure 5:
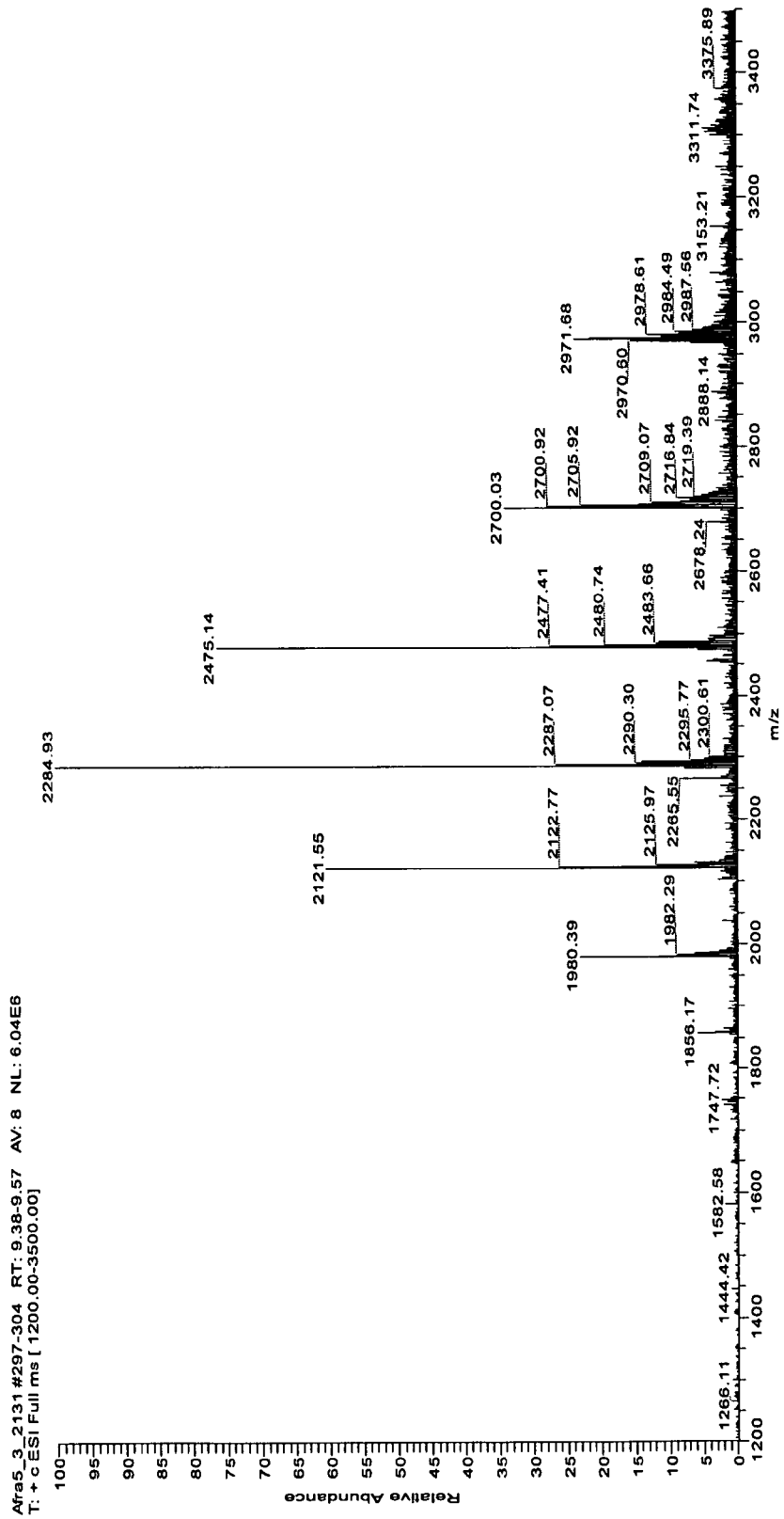
FIG. 5 shows a Multicharge MS spectrum of [DIM3]PlGF-1.
Figure 6:
FIG. 6 shows a deconvoluted mass spectrum of [DIM3] PlGF-1.

The results of this analysis are shown in FIG. 4, and demonstrate a substantially complete re-oxidation resulting in a single purified protein species (see the sharp chromatographic peak at retention time: 9.88 min.). The related multicharge spectrum (FIG. 5) further highlights the absolute prevalence of only one highly pure protein. The identity of this single species as a PlGF-1 homodimer with a molecular weight of 29690±15 Da (theoretical MW=29702) was further confirmed by the deconvoluted mass spectrum of the product (FIG. 6).

Summarizing the results of the HPLC-MS analysis, the product [DIM3]PlGF-1 consists of a prevalent species, which is different from [DIM1/2]PlGF-1. The main differences have been inferred by:

a)—the HPLC analysis that allowed the determination of a different retention time for the two products ([DIM3]PlGF-1 rt=9.88 min) vs [DIM1/2]PlGF-1 rt=7.91 min);

b)—the HPLC-MS spectrum of [DIM3]PlGF-1 that confirmed the obtainment of a single homodimeric protein species with a molecular weight corresponding to the theoretical weight (29700 Da). This contrasts to [DIM1/2]PlGF-1 which consists of a heterogenic protein mixture (19.7-30.5 kDa).

The presence of inter-chain disulfide bridges for the dimeric protein, i.e., the absence of free cysteine thiol-groups, was verified by the Ellman procedure. No free cysteine-thiols were detected in [DIM3]PlGF-1.

These results were further confirmed by the mass analysis of a [DIM3]PlGF-1 sample alkylated with iodoacetamide. The absence of alkylation indicated the complete absence of free cysteine-thiol residue in [DIM3]PlGF-1.

Figure 7:
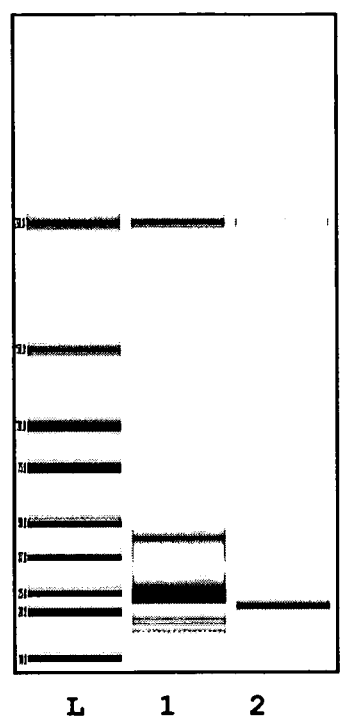
FIG. 7 shows a SDS-PAGE wherein lane L corresponds to the MW standard, lane 1 corresponds to [DIM1/2]PlGF-1 and lane 2 to [DIM3]PlGF-1.

Finally, the SDS-PAGE analysis (FIG. 7) confirmed the intrinsic high purity of the [DIM3]PlGF-1. SDS-PAGE analysis of [DIM3]PlGF-1 as well as of [DIM1/2]PlGF-1 was performed using an automated chip system (Bio-Rad Experion). As shown in FIG. 7, [DIM3]PlGF-1 is significantly more pure than [DIM1/2]PlGF-1. No bands attributable to new products, generated after the purification protocol, were detectable.

The presence of the third interchain disulfide bridge was confirmed also by a tryptic mapping performed in non-reducing conditions and following classical procedures.

All together, these data confirm the presence of three interchain disulfide bridges in the highly pure protein [DIM3] PlGF-1.

Example 3

Production of [DIM3]PlGF-1

2.5 mL of purified DIM1/2 PlGF-1, according to WO-A-03/066676, (conc. 4.5 mg/mL, pH 7.2) are reduced with 20.8 µL of dithiotreitol (DTT) (30.7 mg/mL) obtaining a reducing agent/protein molar ratio of 11/1 (reduction time: 120 min). Following this reaction, the interchain disulfide bridges are reduced, while intrachain disulfide bridges remain intact, thus obtaining PlGF in monomeric form. The reduced protein solution (2.5 mL) is then loaded on PD-10 columns in order to eliminate the reducing agent, and eluted with 3 mL of 50 mM $NaH_2PO_4$ buffer at pH 7.2. The obtained solution is incubated for 48 hours at room temperature.

The product obtained has been characterized as described in Example 2, obtaining equivalent results that prove the formation of a dimer containing three interchain disulfide bonds.

Example 4

Production of [DIM3]PlGF-1

1 mL of purified DIM1/2 PlGF-1, according to WO-A-03/066676, (conc. 0.9 mg/mL, pH 7.2) is reduced with 5 µL of dithiotreitol (DTT) (30.7 mg/mL) obtaining a reducing agent/protein molar ratio of 33/1 (reduction time: 60 min). Following this reaction, the interchain disulfide bridges are reduced, while intrachain disulfide bridges remain intact, obtaining PlGF in monomeric form. A buffer exchange is carried out, in order to eliminate all the redox species from the protein solution as well as to change the buffer to 100 mM TRIS buffer at pH 8.3. In details, the buffer exchange is carried out through centrifuge filtering system Amicon Microcon YM-10, with cut-off of 10.000. 5 filtration cycles are carried out at 10000 g, using an Eppendorf centrifuge, following which 98-99% of molecule with MW under 10.000 Da are eliminated. The obtained solution is incubated for 48 hours at room temperature.

The product obtained has been characterized as described in Example 2, obtaining equivalent results that prove the formation of a dimer containing three interchain disulfide bonds.

Example 5

Production of [DIM3]PlGF-1

1 mL of purified DIM1/2 PlGF-1 (conc. 4.5 mg/mL, pH 7.2) is reduced with 15 µL of dithiotreitol (DTT) (61.7 mg/mL) obtaining a reducing agent/protein molar ratio of 40/1 (reduction time: 60 min). Following this reaction, the interchain disulfide bridges are reduced, while intrachain disulfide bridges remain intact, obtaining PlGF-1 in monomeric form. A buffer exchange is carried out, in order to eliminate all the redox species from the protein solution as well as to change the buffer to 100 mM TRIS buffer at pH 8.3. The buffer exchange is carried out trough centrifuge filtering system Amicon Microcon YM-10, with cut-off of 10.000. 5 filtration cycles are carried out at 10000 g, using an Eppendorf centrifuge, following which 98-99% of molecule with MW under 10.000 Da are eliminated. The obtained solution is incubated for 48 hours at room temperature.

The product obtained has been characterized as described in Example 2, obtaining equivalent results that prove the formation of a dimer containing three interchain disulfide bonds.

Example 6

Production of [DIM3]PlGF-1

3 mL of purified DIM1/2 PlGF-1 (conc. 0.9 mg/mL, pH 7.2) are reduced with 10 µL of dithiotreitol (DTT) (13.3 mg/mL) obtaining a reducing agent/protein molar ratio of 10/1 (reduction time: 100 min). Following this reaction, the interchain disulfide bridges are reduced, while intrachain disulfide bridges remain intact, obtaining PlGF in monomeric form. 2.5 mL of the reduced protein solution are loaded on PD-10 columns in order to eliminate the reducing agent, as well as to carry out a buffer exchange, and the sample is eluted with 3 mL of 50 mM $NH_4H_2PO_4$ at pH 9. The obtained solution is incubated for 24 hours at room temperature.

The product obtained has been characterized as described in Example 2, obtaining equivalent results that prove the formation of a dimer containing three interchain disulfide bonds.

Example 7

Production of [DIM3]PlGF-1 from Inclusion Bodies

A sufficient quantity of inclusion bodies are dissolved in Tris*HCl buffer 50 mM pH 8, containing urea 8M and ethylen diamine 20 mM, to obtain PlGF-1 at the final concentration of roughly 1 mg/mL. 3 mL of the above solution is reduced with 10 µL of dithiotreitol (DTT) (13.3 mg/mL) obtaining a reducing agent/protein molar ratio of 10/1 (reduction time: 100 min). Following this reaction, it is obtained PlGF-1 in a solubilized monomeric form. 2.5 mL of the reduced protein solution are dialyzed for 16 hours at room temperature against 20 volumes of 50 mM $NH_4H_2PO_4$ at pH 9.2 in order to eliminate the reducing and denaturing agents.

The product obtained has been characterized as described in Example 2, obtaining equivalent results that prove the formation of a dimer containing three interchain disulfide bonds.

Example 8

Production of [DIM3]PlGF-1 from Inclusion Bodies

A sufficient quantity of inclusion bodies are dissolved in Tris*HCl buffer 50 mM pH 8, containing urea 8M and ethylen diamine 20 mM, to obtain PlGF-1 at the final concentration of roughly 1 mg/mL. 3 mL of the above solution is reduced with 10 µL of dithiotreitol (DTT) (13.3 mg/mL) obtaining a reducing agent/protein molar ratio of 10/1 (reduction time: 100 min). Following this reaction, it is obtained PlGF-1 in a solubilized monomeric form. 2.5 mL of the reduced protein solution are loaded on PD-10 columns in order to eliminate the reducing and denaturing agents, as well as to carry out a buffer exchange, and the sample is eluted with 3 mL of 50 mM $NH_4H_2PO_4$ at pH 9.2. The obtained solution is further incubated for 24 hours at room temperature.

The product obtained has been characterized as described in Example 2, obtaining equivalent results that prove the formation of a dimer containing three interchain disulfide bonds.

Example 9

Production of [DIM3]PlGF-1 from Inclusion Bodies 2.5 mL of purified DIM1/2 PlGF-1, according to WO-A-03/066676, (conc. 4.5 mg/mL, pH 7.2) are reduced with 20.8 µL of dithiotreitol (DTT) (30.7 mg/mL) obtaining a reducing agent/protein molar ratio of 11/1 (reduction time: 120 min). Following this reaction the interchain disulfide bridges are reduced, while intrachain disulfide bridges remain intact, obtaining PlGF in monomeric form. 2.5 mL of the reduced protein solution are loaded on PD-10 columns in order to eliminate the reducing agent and, in order to carry out a buffer exchange, the sample is eluted with 3 mL of 50 mM $NH_4H_2PO_4$ at pH 9. The obtained solution is incubated for 24 hours at room temperature.

The product obtained has been characterized as described in Example 2, obtaining equivalent results that prove the formation of a dimer containing three interchain disulfide bonds.

Example 10

Stability Assessment

A sample of [DIM3]PlGF-1, obtained as described in anyone of Example 2 to 7, and a sample of DIM1/2 were stored for one month at room temperature. The samples were analyzed by HPLC-UV (to verify the concentration of the protein in the solution) and by HPLC-MS (to verify the integrity of the samples). The results obtained have shown that [DIM3] PlGF-1 is stable at the tested conditions; in fact, neither protein precipitation nor modifications in the structure are detectable. Contrary thereto, a partial precipitation in the DIM1/2 protein sample has been observed.

Example 11

Chemotaxis Assay

The cells used for testing the efficacy of [DIM1/2]PLGF-1 and [DIM3]PlGF-1, were obtained from buffy coats of heparinized blood from normal volunteers through the courtesy of Centro Trasfusionale, Ospedale S. Salvatore, L'Aquila, Italy. Mononuclear cells were obtained by centrifugation on Ficoll/Hipaque. Cellular viability was >95% in all experiments, as measured by trypan blue dye exclusion. Monocyte migration was evaluated using a 48-well micro-chemotaxis chamber, as previously described (Bizzarri C. et al. *Biochem. Pharm.*, 2001, 61, 1429-1437). Briefly, 29 µl of control medium (PBS+0.2% BSA) or increasing concentration of protein solutions were seeded in the lower compartment of the chemotaxis chamber. 50 µl of cells suspension ($3 \times 10^6$ PBMCs/ml) were seeded in the upper compartment. The two compartments of the chemotactic chamber were separated by a 5-µm polycarbonate filter. The chamber was incubated at 37° C. in air with 5% $CO_2$ for 2 hr. At the end of incubation, filters were removed, fixed, stained with Diff-Quik and five oil immersion fields at high magnification (100×) were counted after sample coding.

[DIM3]PlGF-1 was compared with the [DIM1/2]PLGF-1 in dose-response experiments.

As depicted in FIG. 8, results show that the chemotaxis is concentration-dependent. In fact, in spite of similar values of $EC_{50}$ for both [DIM3]PlGF-1 and [DIM1/2]PlGF-1 (0.11 nM vs. 0.15 nM), a higher intrinsic activity in this in vitro assay is evident for [DIM3]PlGF-1. This higher activity demonstrates a greater ability to produce the biological chemotactic effect compared to [DIM1/2]PlGF-1.

Example 12

Mobilization and Colony-Forming Cell Assays

A further and very important confirmation of the improved biological activity of [DIM3]PlGF-1 was obtained in an animal model (BALB/c mice) that allows simulation of PBMC mobilization as in a clinical situation.

The mobilization protocol consisted of i.p. injection of recombinant human granulocyte colony stimulating factor (rhG-CSF; 10 µg/day on days 1-5) in six- to eight-weeks-old-female BALB/c mice (body weight 20-25 g). Combination treatments consisted of 5-day treatments with rhG-CSF (10 µg/day) plus either [DIM1/2]PlGF-1 (5, 10 or 15 µg/day) or [DIM3]PlGF-1 (1.7, 3.3 or 5 µg/day). The dose ranges of PlGF-1 used in combination studies were identified in preliminary experiments. Each experiment was performed on at least three times and the animals were sacrificed 2-3 h after the last treatment. Peripheral blood was harvested into heparin-containing tubes and after WBC counting, diluted with PBS, and mononuclear cells separated by centrifugation on Ficoll discontinuous gradient. Total colony-forming cells (CFCs) were assessed in methylcellulose cultures as described (Carlo-Stella C. et al., *Cancer Res.*, 2002, 62, 6152-6157).

The results obtained show that [DIM3]PlGF-1 synergizes with G-CSF in enhancing the frequencies and the absolute numbers of a broad spectrum of circulating hematopoietic progenitors, including committed colony-forming cells (CFCs), high-proliferative potential-CFCs (HPP-CFCs), primitive long-term culture-initiating cells (LTC-ICs) and radio protective cells. In details, FIG. 9 shows the effect of a combination of G-CSF and [DIM3]PlGF-1 in comparison with the combination of G-CSF with [DIM1/2]PlGF-1 in the increase of CFC/ml numbers, a parameter describing the hematopoietic activity.

As can be observed, both the combinations with [DIM1/2] or [DIM3]PlGF-1 strongly synergize the G-CSF effect in increasing the number/ml of CFCs of at least threefold, as compared with G-CSF alone. However, surprisingly, this effect is obtained at a significantly lower concentration of [DIM3]PlGF-1 compared to [DIM1/2]PlGF ([DIM3]PlGF-1/[DIM1/2]PlGF-1 dose ratio 1:3). This clearly illustrates the higher hematopoietic activity of [DIM3]PlGF-1 compared to [DIM1/2]PlGF-1, both in combination with G-CSF.

Example 13

Evaluation of the Angiogenic Activity of [DIM3]PlGF-1

The angiogenic activity of the [DIM3]PlGF-1, of the [DIM1/2]PLGF-1 factor and, as a positive reference, of the basic fibroblast growth factor (bFGF) were compared using the chicken chorioallantoid membrane vascularization test (CAM) already described by Maglione et al. ("Il Farmaco" supra). Various amounts of [DIM3]PlGF-1 and [DIM1/2] PlGF-1 (between 0 and 3 mcg/sponge) were absorbed on 1 $mm^3$ gelatine sponges, subsequently implanted on the surface of CAMs. After 12 days, the CAM regions in contact with the samples were sectioned, colored and the angiogenic effect was quantified using the morphometric technique known as "point counting". Specifically, the CAM sections were analyzed under a microscope on a grid with 144 intersection points and the results were expressed as the percentage of the intersection points occupied by the capillaries on a transversal section (percentage of the area that is vascularized). The results show (FIG. 10) essentially equivalent angiogenic activity for the [DIM3]PlGF-1 AND [DIM1/2]PlGF-1.

Example 14

Evaluation of the Effect of [DIM3]PlGF-1 on Isoprenaline-Induced Cardiac Ischemia The effect of [DIM3]PlGF-1 on cardiac ischemia and infarct may be evaluated on ischemia induced in an animal model by means of isoprenaline, as described by Maglione et al. (supra) in relation to the wild type factor. The experiment is carried out on rabbits, which are treated with a single daily dose of 160 mcg/Kg of [DIM3]PlGF-1 or with equivalent volumes of excipient only, administered intravenously on days 1 to 5. The Isoprenaline is administered subcutaneously on days 1 and 2. The characteristics typical of the electrocardiogram (ECG) indicating the main ischemic damage, such as inversion of the T wave, widening of the S wave and prominence of the Q wave, are monitored. Variations in the ECG of treated and untreated animals are evaluated on a point scale ranging from zero to six, as reported below:

0, no lesion; 1, prominence of the S wave; 2, prominence of the T wave; 3, depression of the descending arm of the T wave; 4, widening of the S wave; 5, inversion of the T wave; 6, prominence of the Q wave. The total area under the curve defined by the ECG points during the 5 days of the test is calculated for treated and untreated animals. The results underlined by the electrocardiographic profile can be confirmed by macro and microscopic observation of the ischemic tissues. Said examination shows the presence of ischemic lesions and histological alterations of moderated severity with respect to the ones observed in the cardiac tissue of animals treated with the excipient only.

Example 15

Evaluation of the effect of [DIM3]PlGF-1 on Neomycin-Induced Scleroderma

The effect of [DIM3]PlGF-1 on neomycin-induced scleroderma may be studied on the animal scleroderma model described by Yamamoto et al. (supra). A first group of C3H mice is treated with bleomycin (100 mcg/ml) injected daily subcutaneously for 3 weeks. Three other groups of C3H mice are likewise treated as above, but 0.1, 1 and 10 mcg/ml of the PlGF-1CG mutein is added to the daily injection, respectively. After 3 weeks treatment, the animals are sacrificed and samples of skin from the treated areas are taken and subjected to histological analysis. The effect of the treatment with [DIM3]PlGF-1 underlines reduction in histological events particular, skin thickening and hydroxiproline levels that can be attributed to cutaneous sclerotization induced by the bleomycin.

The invention claimed is:
1. An isolated Placental Growth Factor-1 (PlGF-1) homodimer comprising two monomer proteins, characterized in that cysteine residues, in each monomer, at position 125 of recombinant PlGF-1 or position 124 of wtPlGF$_{131}$ of the two monomer proteins forming said homodimer are involved in an intermonomer disulfide bond; wherein (1) PlGF-1 proteins, which contain less than three interchain disulfide bonds, are incubated with a reducing agent and (2) PlGF-1 monomer proteins are oxidized to form said intermonomer disulfide bond, thus obtaining said PlGF-1 homodimer.

2. The PlGF-1 homodimer according to claim 1, characterized in that said homodimer contains three intermonomer disulfide bridges.

3. The PlGF-1 homodimer according to claim 2, characterized in that PlGF-1 is recombinant PlGF-1 and said disulfide bridges are between $Cys^{60}$-$Cys^{69}$, $Cys^{69}$-$Cys^{60}$ and $Cys^{125}$-$Cys^{125}$.

4. A process for preparation of a PlGF-1 homodimer according to claim 1 comprising the following steps:
   I. obtaining PlGF-1 monomer proteins;
   II. allowing said monomer proteins to oxidize by incubating in a buffer having from neutral to basic pH and/or by removing or inactivating any reducing agents, if present, such that they do not interfere with oxidation, thus obtaining the PlGF-1 homodimer; and optionally
   III. purifying the PlGF-1 homodimer.

5. The process according to claim 4, wherein said step I comprises incubating a PlGF-1 homodimer containing less than three interchain disulfide bridges in a buffer containing a reducing agent and having from neutral to basic pH, thus obtaining the PlGF monomer protein.

6. The process according to claim 4, wherein said step I comprises incubating bacterial inclusion bodies containing PlGF-1 in a buffer containing a denaturing agent and reducing the thus obtained protein solution with a reducing agent.

7. The process according to claim 4, wherein said reducing agent is selected from the group comprising Tris (2-Carboxyethyl) phosphine Hydrochloride (TCEP*HCl), Dithiothreitol (DTT) and a mixture thereof.

8. The process according to claim 4, wherein said reducing agent is used at a molar ratio reducing agent/PlGF protein in the range 5:1-100:1.

9. The process according to claim 4, wherein incubation with said reducing agent is carried out for a time ranging from 10 to 30 hours.

10. The process according to claim 4, additionally comprising purifying the PlGF-1 monomer proteins.

11. The process according to claim 4, wherein the oxidation in step II is carried out by incubating in a buffer at a temperature comprised between 15° and 30° C. degrees.

12. The process according to claim 11, wherein said oxidation is carried out for a time comprised between 12 and 48 hours.

13. The process according to claim 4, wherein removing or inactivating the reducing agent in step II is carried out by diluting, dialyzing or replacing the buffer with a buffer not containing any reducing agent.

14. The process according to claim 4, wherein removing the reducing agent is carried out by purifying the monomer.

15. The process according to claim 4, wherein said purifying in step III is carried out by chromatographic purification.

16. A method for promoting mobilization of blood stem cells, inducing angiogenesis, or stimulating migration of endothelial cells, the method comprising administering a PlGF-1 homodimer according to claim 1 to a subject in need thereof.

17. The method according to claim 16, wherein said subject is a post-operative patient.

18. The method according to claim 16, wherein said subject is a patient undergoing chemotherapy.

19. The method according to claim 16, wherein said subject has ischemic disease.

20. The method according to claim 19, wherein the ischemic disease is selected from the group consisting of myocardial tissue ischemia, myocardial infarct, ischemic ictus and chronic ischemic myocardial diseases cerebral ischemia and ischemic ictus, intestinal ischemia, and peripheral ischemia of the limbs.

21. The method according to claim 16, wherein said subject has cutaneous scleroderma or progressive systemic scleroderma.

22. The method according to claim 21, wherein scleroderma is myocardial scleroderma.

23. The method according to claim 16, wherein said subject has skin ulcers, wounds, or burns.

24. The method according to claim 16, wherein said subject has natural or precocious ageing of cutaneous tissues.

25. The method according to claim 16, wherein said subject has pathological hair loss.

26. Pharmaceutical composition comprising a PlGF-1 homodimer according to claim 1 in admixture with at least a pharmaceutically acceptable excipient.

* * * * *